(12) United States Patent
Kant et al.

(10) Patent No.: US 12,083,143 B2
(45) Date of Patent: Sep. 10, 2024

(54) MLK-REGULATED microRNAS IN ANGIOGENESIS AND TUMOR DEVELOPMENT

(71) Applicant: University of Massachusetts, Boston, MA (US)

(72) Inventors: Shashi Kant, Shrewsbury, MA (US); Siobhan Craige, Christiansburg, VA (US); John F. Keaney, Jr., Hingham, MA (US); Roger J. Davis, Princeton, MA (US)

(73) Assignee: University of Massachusetts, Boston, MA (US)

( * ) Notice: Subject to any disclaimer, the term of this patent is extended or adjusted under 35 U.S.C. 154(b) by 949 days.

(21) Appl. No.: 17/045,327

(22) PCT Filed: Apr. 5, 2019

(86) PCT No.: PCT/US2019/026117
§ 371 (c)(1),
(2) Date: Oct. 5, 2020

(87) PCT Pub. No.: WO2019/195765
PCT Pub. Date: Oct. 10, 2019

(65) Prior Publication Data
US 2021/0023118 A1    Jan. 28, 2021

Related U.S. Application Data

(60) Provisional application No. 62/653,876, filed on Apr. 6, 2018.

(51) Int. Cl.
| *C07H 21/02* | (2006.01) |
| *A61K 31/553* | (2006.01) |
| *A61K 31/713* | (2006.01) |
| *A61P 35/00* | (2006.01) |
| *C07H 21/04* | (2006.01) |
| *C12N 15/113* | (2010.01) |

(52) U.S. Cl.
CPC .......... *A61K 31/713* (2013.01); *A61K 31/553* (2013.01); *A61P 35/00* (2018.01); *C12N 15/1135* (2013.01); *C12N 2310/141* (2013.01); *C12N 2320/30* (2013.01); *C12N 2320/31* (2013.01); *C12Y 207/11025* (2013.01)

(58) Field of Classification Search
CPC .......................... C12N 15/113; C12N 2310/141
See application file for complete search history.

(56) References Cited

U.S. PATENT DOCUMENTS

| 5,716,928 A | 2/1998 | Benet et al. |
| 5,858,401 A | 1/1999 | Bbalani et al. |
| 6,007,839 A | 12/1999 | Mayhew et al. |
| 6,063,400 A | 5/2000 | Geho et al. |
| 9,061,009 B2 | 6/2015 | Davis et al. |
| 2004/0028670 A1 | 2/2004 | Carlson et al. |
| 2005/0209299 A1 | 9/2005 | Shapiro |
| 2010/0215665 A1 | 8/2010 | Davis et al. |
| 2010/0286378 A1 | 11/2010 | Li et al. |
| 2014/0363469 A1 | 12/2014 | Meyers et al. |
| 2015/0225716 A1* | 8/2015 | Brakenhoff ............. A61P 35/00 435/6.12 |
| 2017/0037404 A1 | 2/2017 | Brown et al. |
| 2017/0252461 A1 | 9/2017 | Chakraborty et al. |

FOREIGN PATENT DOCUMENTS

| CA | 3068585 A1 * | 1/2019 | ........... C12N 15/113 |
| WO | WO 2013/079701 A2 * | 6/2013 | ....... C12N 2310/141 |
| WO | WO 2016/149370 | 9/2016 | |
| WO | WO 2016/201370 | 12/2016 | |

OTHER PUBLICATIONS

Son et al. (Tuberc Respir Dis 2009;67:413-421).*
Al-Muhammed et al., "In-vivo studies on dexamethasone sodium phosphate liposomes," Journal of Microencapsulation, Jan. 1, 1996, 13(3):293-305.
Aragones et al., "Pharmacokinetics of oestrone-3-O-sulphamate. The Journal of Steroid Biochemistry and Molecular Biology," Aug. 1, 1996, 58(5-6):611-7.
Brophy et al., "Bioavailability of oral dexamethasone during high dose steroid therapy in neurological patients," European Journal of Clinical Pharmacology, Jan. 1, 1983, 24(1):103-8.
Chadee et al., "Involvement of mixed lineage kinase 3 in cancer," Canadian Journal of Physiology and Pharmacology, Dec. 13, 2012, 91(4):268-74.
Chen et al., "miR-146a inhibits cell growth, cell migration and induces apoptosis in non-small cell lung cancer cells. PloS one," Mar. 26, 2013, 8(3):e60317.
Chen et al., "MLK3 is critical for breast cancer cell migration and promotes a malignant phenotype in mammary epithelial cells," Oncogene, Aug. 2010, 29(31):4399-411.
Chen et al., "MLK3 regulates paxillin phosphorylation in chemokine-mediated breast cancer cell migration and invasion to drive metastasis," Cancer Research, Aug. 15, 2012, 72(16):4130-40.
Chonn et al., "Recent advances in liposomal drug-delivery systems," Current Opinion in Biotechnology, Jan. 1, 1995, 6(6):698-708.
Craige et al., "Mixed-lineage protein kinases (MLKs) in inflammation, metabolism, and other disease states," Biochimica et Biophysica Acta (BBA)—Molecular Basis of Disease, Sep. 1, 2016, 1862(9):1581-6.
Eyles et al., "Oral Delivery and Fate of Poly (lactic acid) Microsphere-encapsulated Interferon in Rats," Journal of Pharmacy and Pharmacology, Jul. 1997, 49(7):669-74.
Fotherby et al., "Bioavailability of orally administered sex steroids used in oral contraception and hormone replacement therapy," Contraception, Aug. 1, 1996, 54(2):59-69.

(Continued)

*Primary Examiner* — Amy Rose Hudson
(74) *Attorney, Agent, or Firm* — Fish & Richardson P.C.

(57) ABSTRACT

Methods for treating cancer, and for reducing angiogenesis in a tissue, comprising administering one or more of a miR-371 oligonucleotide; a miR-146 oligonucleotide; or an inhibitor of MLK2/3 activity.

3 Claims, 18 Drawing Sheets
Specification includes a Sequence Listing.

(56) References Cited

OTHER PUBLICATIONS

Gallo et al., "Mixed-lineage kinase control of JNK and p38 MAPK pathways," Nature Reviews Molecular Cell Biology, Sep. 2002, 3(9):663-72.
Gao et al., "Controlled release of a contraceptive steroid from biodegradable and injectable gel formulations: in vitro evaluation," Pharmaceutical Research, Jun. 1, 1995, 12(6):857-63.
Houbaviy et al., "Characterization of a highly variable eutherian microRNA gene," Rna, Aug. 1, 2005, 11(8):1245-57.
Johnson et al., "Permeation of steroids through human skin," Journal of Pharmaceutical Sciences, Sep. 1, 1995, 84(9):1144-6.
Li et al., "Functions of miR-146a and miR-222 in tumor-associated macrophages in breast cancer," Scientific Reports, Dec. 22, 2015, 5:18648, 15 pages.
Marson et al., "Connecting microRNA genes to the core transcriptional regulatory circuitry of embryonic stem cells," Cell, Aug. 8, 2008, 134(3):521-33.
Medeiros et al., "Mir-290-295 deficiency in mice results in partially penetrant embryonic lethality and germ cell defects," Proceedings of the National Academy of Sciences, Aug. 23, 2011, 108(34):14163-8.
Minto et al., "Pharmacokinetics and pharmacodynamics of nandrolone esters in oil vehicle: effects of ester, injection site and injection volume," Journal of Pharmacology and Experimental Therapeutics, Apr. 1, 1997, 281(1):93-102.
Ostro et al., "Use of liposomes as injectable-drug delivery systems," American Journal of Health-System Pharmacy, Aug. 1, 1989, 46(8):1576-88.
Panduranga Rao, "Recent developments of collagen-based materials for medical applications and drug delivery systems," Journal of Biomaterials Science, Polymer Edition, Jan. 1, 1996, 7(7):623-45.
PCT International Preliminary Report on Patentability in International Appln. No. PCT/US2019/026117, dated Oct. 6, 2020, 9 pages.
PCT International Search Report and Written Opinion in International Appln. No. PCT/US2019/026117, dated Jun. 27, 2019, 14 pages.
Ramo et al., "Suppression of ischemia in arterial occlusive disease by JNK-promoted native collateral artery development," Elife, Aug. 9, 2016, 5:e18414, 61 pages.
Rohatagi et al., "Pharmacokinetic and pharmacodynamic evaluation of triamcinolone acetonide after intravenous, oral, and inhaled administration," The Journal of Clinical Pharmacology, Dec. 1995, 35(12):1187-93.
Shenouda et al., "MicroRNA function in cancer: oncogene or a tumor suppressor?," Cancer and Metastasis Reviews, Dec. 1, 2009, 28(3-4):369, 10 pages.
Wang et al., "Embryonic stem cell-specific microRNAs regulate the G1-S transition and promote rapid proliferation," Nature Genetics, Dec. 2008, 40(12):1478-83.
Widlansky et al., "The clinical implications of endothelial dysfunction," Journal of the American College of Cardiology, Oct. 1, 2003, 42(7):1149-60.
Zhan et al., "Mixed lineage kinase 3 is required for matrix metalloproteinase expression and invasion in ovarian cancer cells." Experimental Cell Research., Aug. 15, 2012, 318(14):1641-8.
Zhang et al., "microRNAs as oncogenes and tumor suppressors," Developmental Biology, Feb. 1, 2007, 302(1):1-2.
Zu et al., "MiR-146a suppresses hepatocellular carcinoma by downregulating TRAF6," American Journal of Cancer Research, 2016, 6(11):2502-13.
Zheng et al., "A latent pro-survival function for the mir-290-295 cluster in mouse embryonic stem cells," PLoS Genetics, May 2011, 7(5):e1002054, 11 pages.
Zhou et al., "miR-146a promotes growth of osteosarcoma cells by targeting ZNRF3/GSK-3β/β-catenin signaling pathway," Oncotarget, Sep. 2017, 8(43):74276, 11 pages.

* cited by examiner

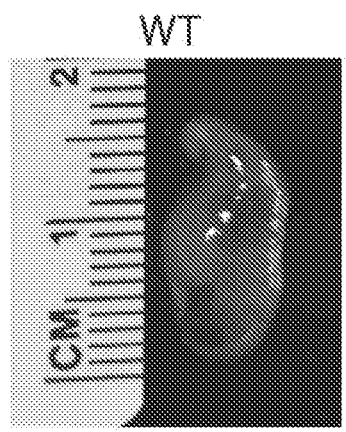
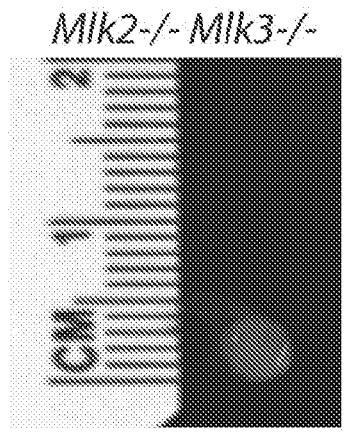
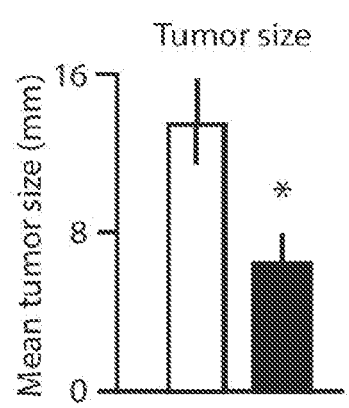
FIG. 4A
FIG. 4B
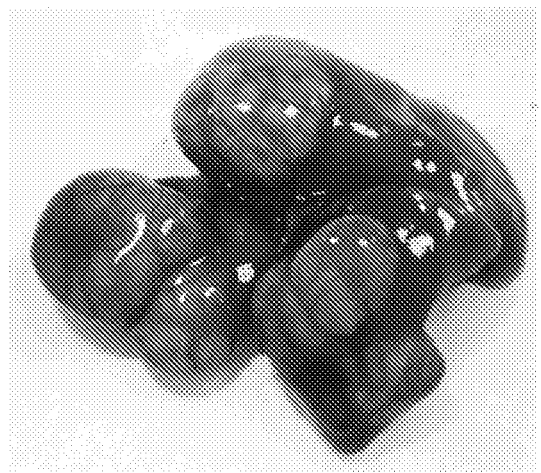
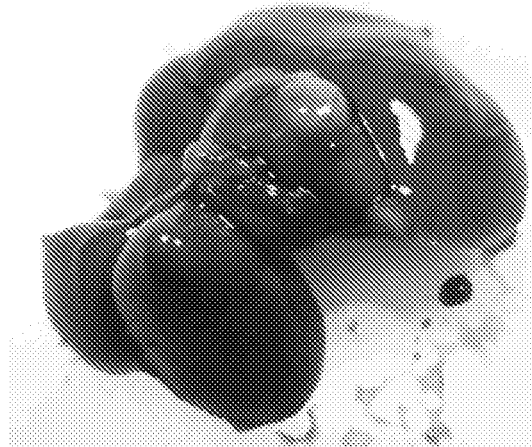
FIG. 5A

Top Analysis-Ready Molecules

Exp Fold Change up-regulated

| Molecules | Exp. Value |
|---|---|
| U90926 | ↑ 5.850 |
| Snord13* | ↑ 5.779 |
| ALDH1A1 | ↑ 5.658 |
| SPP1 | ↑ 5.625 |
| SPARCL1 | ↑ 4.776 |
| Mir290b | ↑ 3.926 |
| Snord14e | ↑ 3.084 |
| SERPINA3* | ↑ 3.053 |
| FGF23 | ↑ 3.019 |
| CDO1 | ↑ 3.004 |

Exp Fold Change down-regulated

| Molecules | Exp. Value |
|---|---|
| Erdr1 | ↓ -11.682 |
| mir-467* | ↓ -6.232 |
| Crisp1/Crisp3* | ↓ -5.519 |
| Vmn1r180 (includes others)* | ↓ -5.285 |
| NTS | ↓ -3.871 |
| MAP3K11 | ↓ -3.781 |
| ADAM8 | ↓ -3.382 |
| POP4 | ↓ -2.824 |
| Htr5b | ↓ -2.707 |
| Ssty1 (includes others)* | ↓ -2.552 |

FIG. 8A

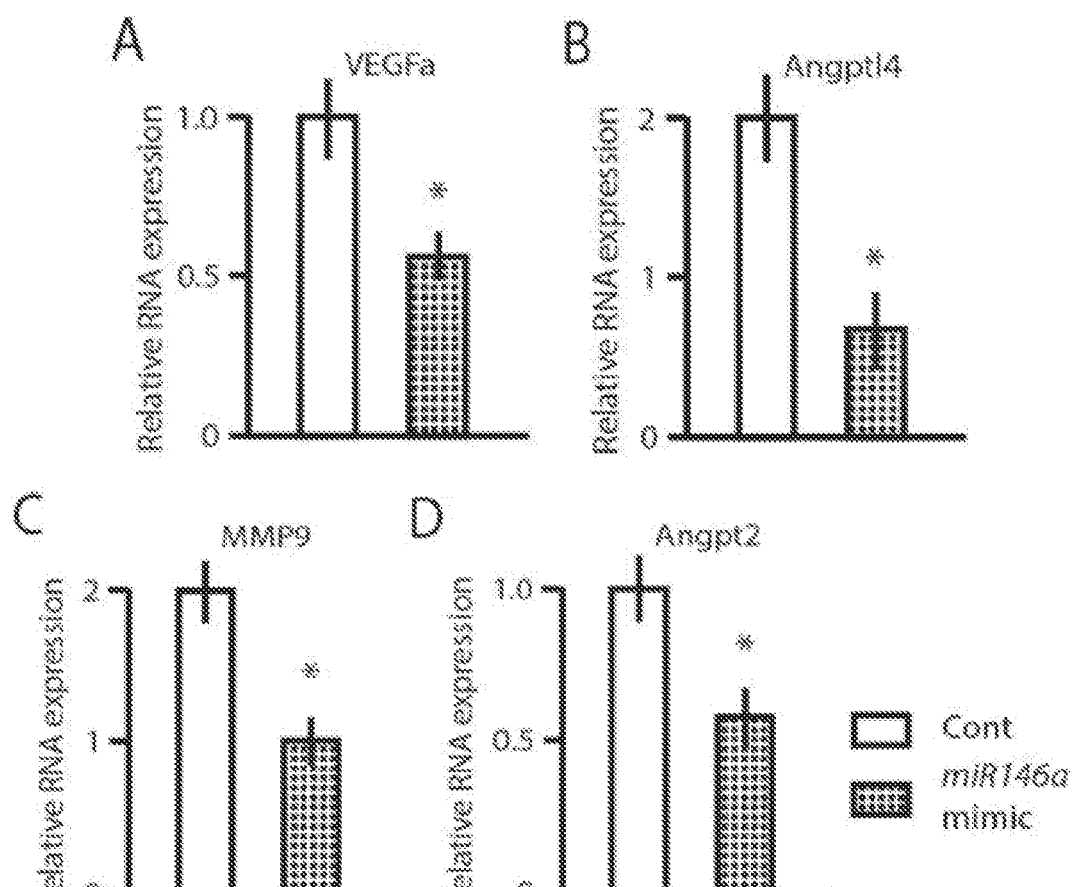
FIGs. 11A-D

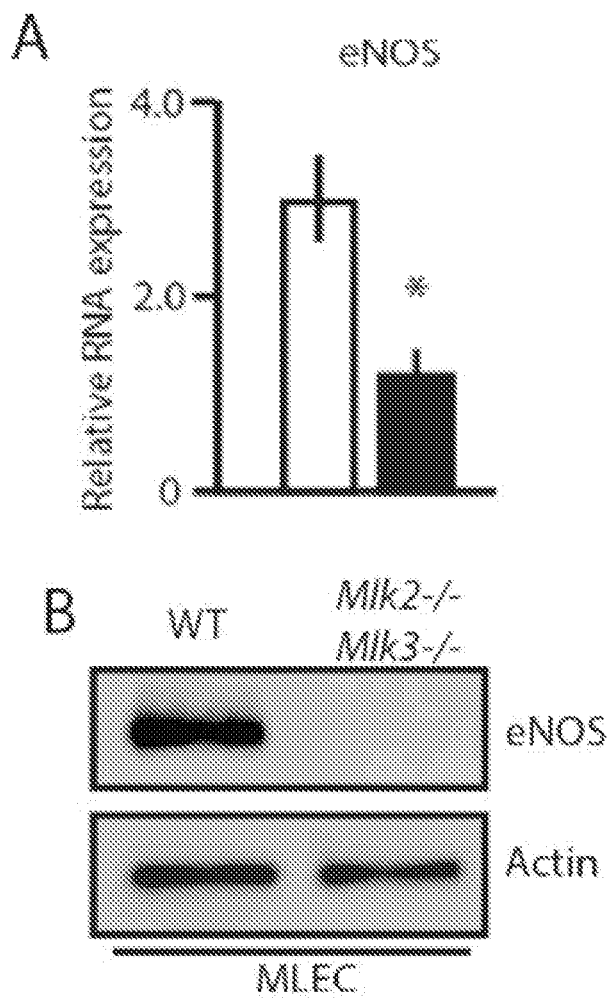
FIGs. 12A-B

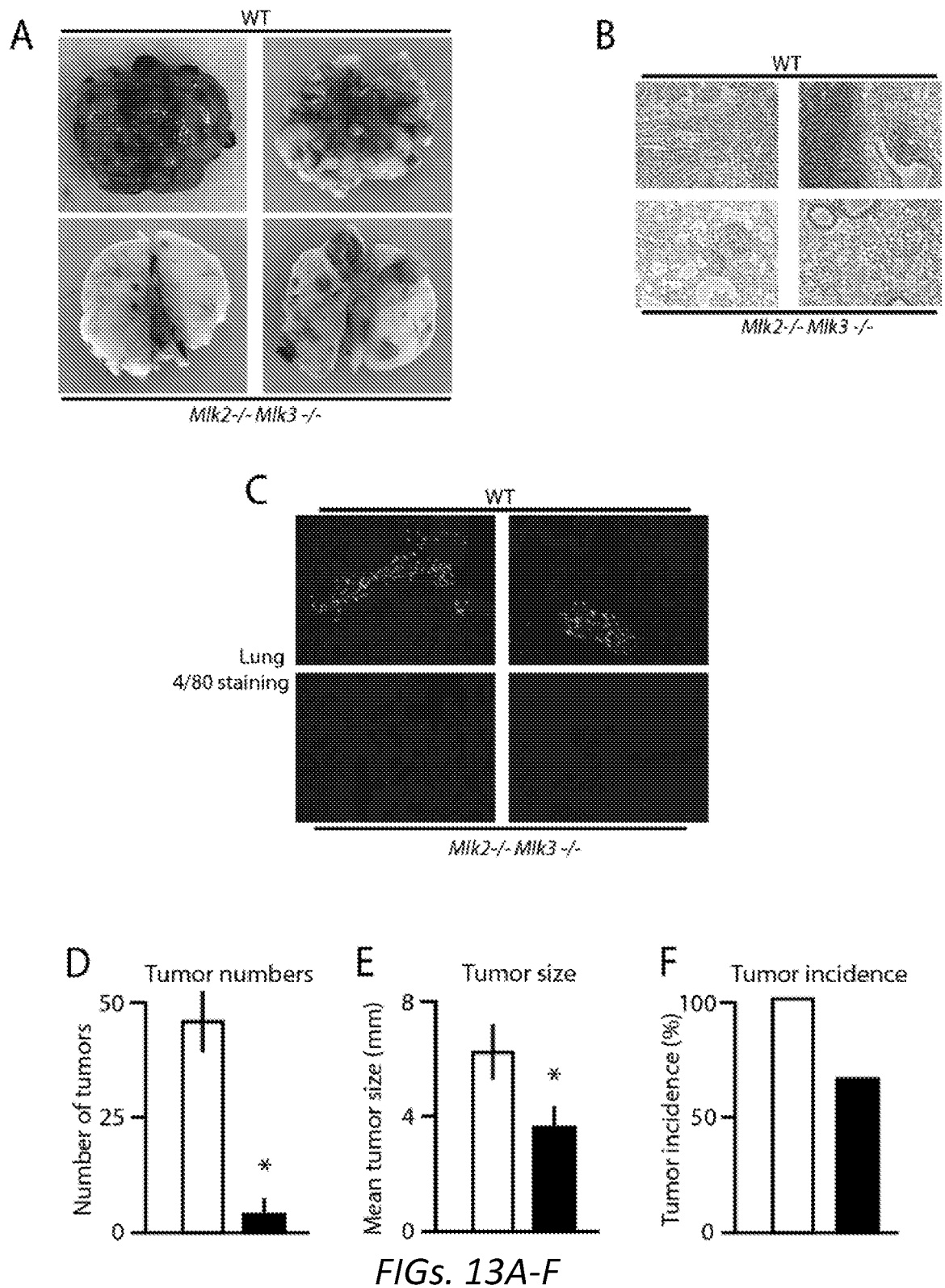
FIGs. 13A-F

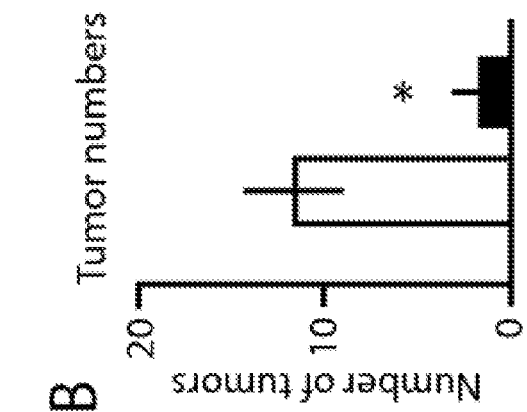
FIGs. 14A-B

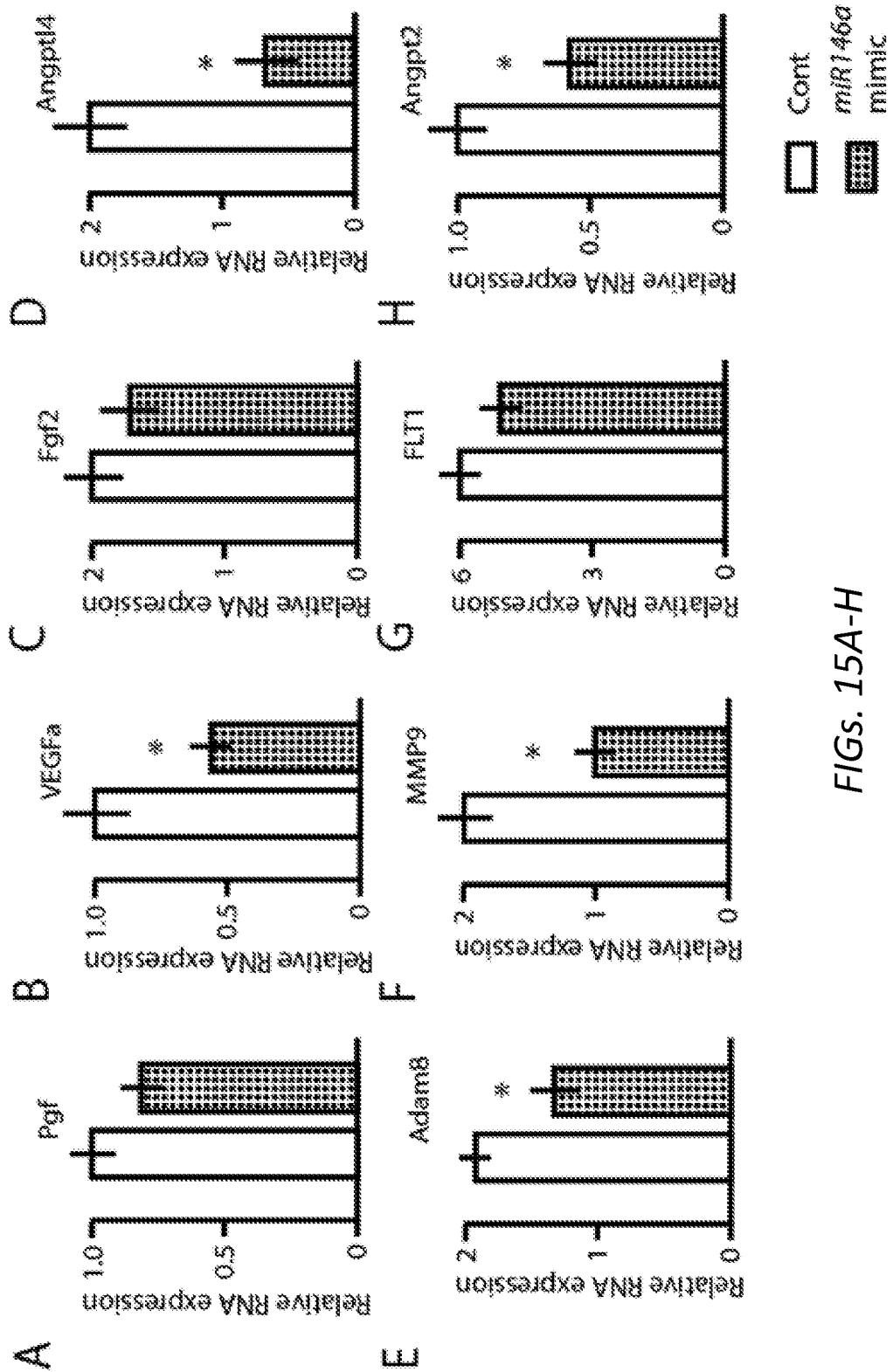
FIGs. 15A-H

MLK-REGULATED microRNAS IN ANGIOGENESIS AND TUMOR DEVELOPMENT

CLAIM OF PRIORITY

This application is a U.S. National Stage Application under 35 USC § 371 of International Patent Application Serial No. PCT/US2019/026117 filed on Apr. 5, 2019, entitled "MLK-Regulated microRNAs in Angiogenesis and Tumor Development," which claims the benefit of U.S. Provisional Patent Application Ser. No. 62/653,876, filed on Apr. 6, 2018. The entire contents of the foregoing are hereby incorporated by reference.

FEDERALLY SPONSORED RESEARCH OR DEVELOPMENT

This invention was made with Government support under Grant Nos. DK089185 and DK107570 awarded by the National Institutes of Health. The Government has certain rights in the invention.

TECHNICAL FIELD

Described herein are methods for treating cancer, and for reducing angiogenesis in a tissue, comprising administering one or more of a miR-290b oligonucleotide; a miR-146 oligonucleotide; or an inhibitor of MLK2/3 activity.

BACKGROUND

Endothelial cells are a key determinant of normal vascular homeostasis and exert control over vascular tone, thrombosis, inflammation, and angiogenesis in response to tissue ischemia.[1] The control of these processes requires endothelial cells to resist injurious stimuli such as reactive oxygen and nitrogen species (ROS/RNS), hypoxia, cytokines and coagulation products. When endothelial resistance to injury is overcome, endothelial dysfunction becomes manifest as defects in homeostatic control of the aforementioned processes.[2] Endothelial dysfunction appears important for human health, as patients with endothelial dysfunction are at increased risk of vascular disease[3,4]. With endothelial dysfunction, processes fundamental for repair and responses to tissue ischemia such as angiogenesis are impaired.[5]

SUMMARY

Described herein are methods for decreasing angiogenesis in a tissue. In some embodiments, preferably wherein the tissue is not a tumor, the methods include delivering to the tissue one or more compositions comprising: a miR 290b oligonucleotide; a miR-146 oligonucleotide; and/or an inhibitor of MLK2/3. In some embodiments, the subject has peripheral artery disease (PAD), Arm artery disease (ARMD), or diabetes.

Also provided herein are methods for treating a solid tumor in a subject. The methods include administering a composition comprising a miR-371 oligonucleotide, wherein the composition is preferably administered locally to the tumor or to the vasculature of the tumor, and wherein the composition is administered in an amount sufficient to inhibit angiogenesis in the tumor. In some embodiments, the solid tumor is a carcinoma, e.g., a lung, liver, or breast carcinoma.

In some embodiments, the miR-371 oligonucleotide comprises hsa-miR-371b-5p, e.g., ACUCAAAAGAUGGCGGCACUUU (SEQ ID NO:1).

In some embodiments, the miR-371 oligonucleotide comprises hsa-miR-371a-5p, e.g., ACUCAAACUGUGGGGGCACU (SEQ ID NO:2).

In some embodiments, the miR-146 oligonucleotide comprises hsa-miR-146a-5p, e.g., UGAGAACUGAAUUCCAUGGGUU (SEQ ID NO:3).

In some embodiments, the miR-146 oligonucleotide comprises hsa-miR-146b-5p, e.g., UGAGAACUGAAUUCCAUAGGCUG (SEQ ID NO:4)

In some embodiments, the inhibitor of MLK2/3 is a small molecule, e.g., an indolocarbazole MLK inhibitor, e.g., CEP-1347, CEP-11004, or K252a; an antibody or antigen binding fragment thereof, e.g., the antibody or antigen binding fragment thereof is an intrabody.

Also provided here is the use of compositions comprising a miR 290b oligonucleotide; a miR-146 oligonucleotide; and/or an inhibitor of MLK2/3 for decreasing angiogenesis, as well as miR-371 oligonucleotides for use in treating a solid tumor.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 4A-B. MLK-deficient mice are protected from Lewis Lung Carcinoma (LLC) Tumor. (A) Lewis Lung Carcinoma (LLC) tumors 12 d after implantation. (B) Composite LLC tumor size, (N=6, p<0.05 vs. WT).

FIGS. 5A-C. MLK-deficient mice are protected from Hepatocellular carcinoma (HCC) tumor. (A) Hepatocellular carcinoma (HCC) tumor size 9 months after DEN injection (N=6, p<0.05). Composite LLC tumor number (B) and tumor size (C) (N=6, p<0.05 vs. WT).

FIGS. 8A-B. miR-290b expression in endothelial cell. A) Bioinformatics analysis (ingenuity pathway analysis (IPA)) of microarray data from MLECs revealed miR290b is one of the most highly upregulated genes in MLK−/− endothelial cells compared to WT. (B) mRNA was isolated from mouse lung endothelial cell (MLEC) and qRT-PCR was performed for miR290b either with or without 4 hours post hypoxia treatment.

FIGS. 11A-D. miR146a overexpression mimic the MLK deficient phenotype. (A-D) mRNA was isolated from WT mouse lung endothelial cell (MLEC) treated either with control or miR146a mimic for 48 hours and qRT-PCR was performed for different angiogenesis related genes after 4 hours post hypoxia FIGS. 12A-B. eNos mRNA and protein expression in endothelial Cell. (A) qPCR was performed in WT (white bar) and MLK deficient mice (black bar). (B) Western blotting was performed in WT and MLK-deficient MLEC.

FIGS. 13A-F. MLKs are required for LLC1 induced Lung tumor in mice. (A) Lung from WT and MLK2/3 knockout mice were isolated to examine the tumor formation after 20 days of LLC1 injection in tail vein of mice (1×10$^6$ LLC1 cells). (B) Lungs were harvested and formalin fixed for histology. We further stained for macrophages in lung tissue (FIG. 13C). LLC tumor number induced tumor size (D), number (E) and incidences (F) were determined (N=6, p<0.05 vs. WT). (WT—White bar; MLK2/3 KO—Black bar).

FIGS. 14A-B. MLK inhibitor (URMC-099) suppressed LLC1 tumor formation in vivo. 1×10$^6$ LLC1 cells, with either MLK inhibitor (URMC-099) or solvent in 200 ul of sterile PBS were injected into the tail vein of WT mice (12-16 week of age). After 20 days of injection Lung was isolated (A) and tumor number were counted (Control—White bar; MLK inhibitor—Black bar) (B).

FIGS. 15A-H. miR146a suppressed the pro-angiogenic factors similar to mir290b. Either control or miR146a mimic were transfected into primary MLEC cells for 48 hours. Cells were incubated for 90 minutes in hypoxia chamber in the presence of 1% O$_2$. RNA was isolated and qPCR was performed for genes as noted.

DETAILED DESCRIPTION

There is a significant need for targeted angiogenic therapy. As described herein, members of the mixed lineage kinase family modulate angiogenesis; in particular, mixed lineage kinases 2 and 3 orchestrate postnatal angiogenesis.

The idea that endothelial Mlk family members (Mlk2/3) are required for normal postnatal endothelial function is new; this disclosure is the first to demonstrate in vivo inhibition of post-natal angiogenesis with deletion of MLK2/3. As shown herein, MLK 2/3 dictates endothelial phenotype post-natally and is required for angiogenesis in solid tumors. MLKs regulate endothelial phenotype via microRNA290b- and 146a-dependent and eNos-dependent mechanisms. This is the first demonstration that miR-290b regulates endothelial (or any cardiovascular) phenotype.

Thus, provided herein are methods for inhibiting the MLK pathway as a treatment for solid tumors, by mimicking miR290b or mir146a.

Mixed Lineage Kinases (MLKs)

Figure 1A:
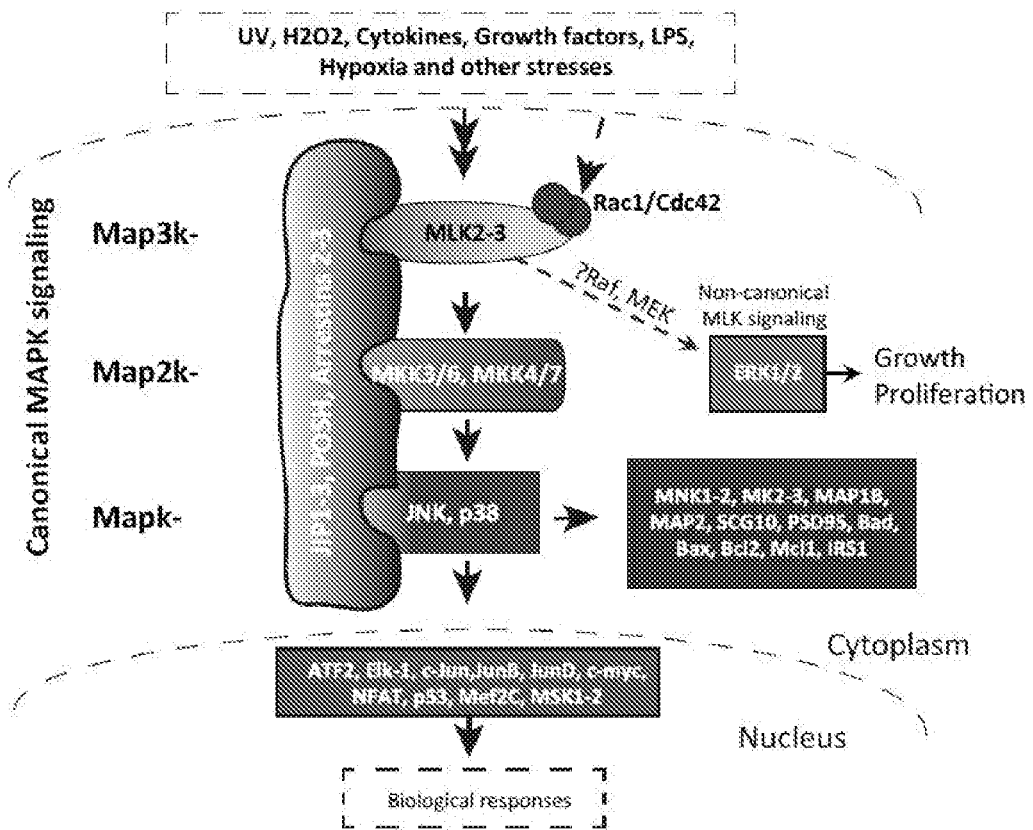
FIGS. 1A-B. The Mixed Lineage Kinase (MLK) pathway. (A) Canonical three tier Mapk signaling is shown on the left. The MLK pathway can be activated by Cdc42/Rac-dependent stimuli. Classic activation prompts contextual binding of MLK-related proteins to a scaffold protein (JIP1-3, POSH, Arrestin2-3) followed by Map2k activation (MKK3/6 or MKK4/7) that, in turn, activates JNK and/or p38 stimulating either cytosolic or nuclear targets as indicated. (B) Structure of MLKS with Src homology (SH3), kinase (K), leucine zipper (LZ), and Cdc42 and Rac interactive binding (CRIB) domains.
Figure 1B:
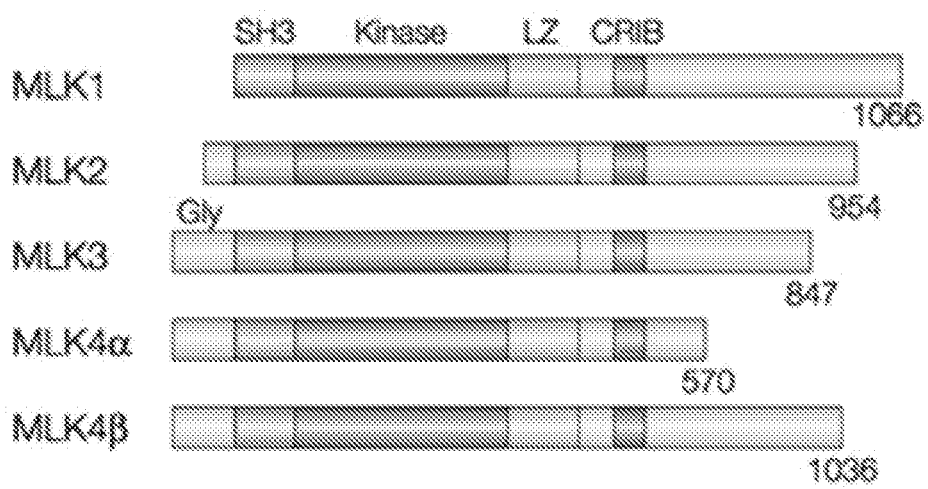
Figure 2:
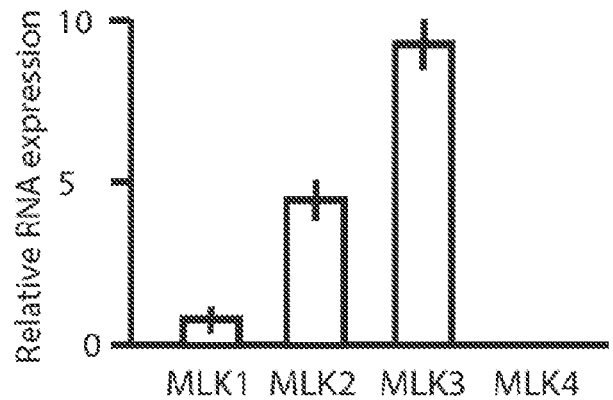
FIG. 2. RNA expression of MLK family members by qPCR in mouse lung endothelial cells.

The mixed lineage kinases (MLKs) are classified in the Ser/Thr MAP kinase family of proteins. However, the sequence homology of their kinase domains demonstrates similarity to both Ser/Thr and Tyr kinases. There are three subfamilies comprised of seven members thus far identified in mammals: the MLK core group, the DLK (dual leucine-zipper bearing kinase) group, and the ZAK (Sterile alpha motif and leucine zipper containing kinase) group (FIG. 1) [1, 2]. The endothelium is involved in sensing and responding to hypoxia [3] to drive new blood vessel formation. In the endothelium, the family members MLK 1, 2, and 3 are expressed, with the latter two expressed significantly more than MLK 1 [4] and data presented herein (FIG. 2).

MLK2/3 have been implicated in cancer cell migration and proliferation in vitro [5-8], with limited data on MLK2/3 in tumor formation or angiogenesis in vivo. In a breast cancer xenograft model, MLK3 shRNA prevented metastasis in mice [6].

MLK2/3 has been shown to be important for developmental collateral formation [4]; the present methods are based on experiments that focused on post-natal angiogenesis in tumor formation. Described herein is a novel path by which MLK2/3 in the endothelium drives angiogenesis in response to hypoxia. During ischemic conditions, tissue hypoxia increases growth factor production leading to endothelial cell proliferation, migration and vessel formation. MLK2/3 dictates angiogenic phenotype in two ways: 1) through control of miRNAs 290b and 146a to control downstream angiogenic mediators (PGF, MMP9, Adam8), and 2) through regulation of eNOS expression. The results described herein demonstrate that micro RNAs 290b and 146a are involved in controlling downstream growth factors necessary for angiogenesis. MicoRNAs play an important role in gene regulation by translational repression, mRNA cleavage, and mRNA decay.

We have found that miR-290, e.g., miR-290b, plays a significant role in controlling hypoxia induced angiogenesis. miR-290b is a unique micro RNA that falls within the eutherian miR-290-295 cluster, which is equivalent to human miR-371-373. Knowledge of the physiological role of miR-290b is sparse; it is on the opposite strand of the mouse miR-290-295 cluster (human miR-371-373) that is related to ES cell maintenance, G1-S cell cycle transition, and germ line formation. The observations herein address for the first time the role of miR-290b role in endothelial function and tumor development [11-14].

MiR146a is also involved in this pathway. Previous literature has described that mir146 may play a role in tumor development [15-17], yet mir-146 has not been described in any context linked to regulation by MLK.

Methods of Treatment

Described herein are methods for treating cancer, and for reducing angiogenesis in a tissue, comprising administering one or more of an inhibitor of MLK2/3 activity; a miR-371 (the human equivalent of mouse miR-290) oligonucleotide; and/or a miR-146 oligonucleotide.

Specific inhibitors of MLK activity are known in the art. For example, the MLK activity inhibitor can be a small molecule, e.g., an indolocarbazole MLK inhibitor, e.g., CEP-1347, CEP-11004, or K252a. In another example, the MLK inhibitor is an antibody or antigen binding fragment thereof, e.g., the antibody or antigen binding fragment thereof is an intrabody. In some embodiments, administration of an antibody includes administering to the subject or one or more cells of the subject a nucleic acid that encodes the antibody. In some embodiments, the MLK inhibitor is an inhibitory nucleic acid, e.g., an antisense oligonucleotide, LNA, PNA, siRNA, or shRNA. See, e.g., U.S. Pat. No. 9,061,009B2.

miR-371 and miR-146 oligonucleotides can include synthetic miRNA oligonucleotides comprising the mature sequence or the precursor sequence of the miRNA, or miRNA mimetics, e.g., as described in WO2016149370 and US20100286378. Although human sequences are exemplified here, sequences from other species can be identified and used in subjects of other species.

miR-371

The human miR-371a stem loop precursor structure is as follows:

```
                    cu    g              u   c
      5'guggcacucaaa  gugg ggcacuuuc gcu u
        |||||||||||| |||| ||||||||| |||
      3'cauugugaguuu  uacc ccgugaaag ugg c
                    uc   g            -   u
```

The 5' and 3' mature miRNAs are shown in bold. The linear sequence is (SEQ ID NO: 5)
GUGGCACUCAAACUGUGGGGGCACUUUCUGCUCUCUGGUGAAAGUGCC

GCCAUCUUUUGAGUGUUAC.

The human miR-371b stem loop precursor structure is as follows:

```
         gguaa       aga    c            acca
       5'     cacucaaa  ugg ggcacuuuc         g
              ||||||||  ||| |||||||||         a
       3'     gugaguuu  acc ccgugaaag         g
         ---cc        gac    c            acga
```

The 5' and 3' mature miRNAs are shown in bold. The linear sequence is (SEQ ID NO: 6)
GGUAACACUCAAAAGAUGGCGGCACUUUCACCAGAGAGCAGAAAGUGC

CCCCACAGUUUGAGUGCC.

In some embodiments, the oligonucleotide comprises miR-371b-5p, e.g., (SEQ ID NO: 1)
ACUCAAAAGAUGGCGGCACUUU, or hsa-miR-371a-5p. e.g., (SEQ ID NO: 2)
ACUCAAACUGUGGGGGCACU.

miR-146

The human miR-1461a stem loop precursor structure is as follows:

```
              c    -----u     u    uu          c   u    g   uc
        5' cgaug      guaucc cagcu gagaacugaauu ca ggguu ug    a
           |||||      |||||| ||||| |||||||||||| || ||||| ||    g
        3' gcuac      uauagg gucga uucuugacuuaa gu uccag ac    u
              u    ugucuc    -    -c           a   c    -   ug
```

The 5' and 3' mature miRNAs are shown in bold. The linear sequence is (SEQ ID NO: 7)
CCGAUGUGUAUCCUCAGCUUUGAGAACUGAAUUCCAUGGGUUGUGUCA

GUGUCAGACCUCUGAAAUUCAGUUCUUCAGCUGGGAUAUCUCUGUCAU

CGU.

The human miR-146b stem loop precursor structure is as follows:

```
                u    g        au        cu   ga  u
       5' cc ggcacu agaacuga uccauagg gu gc c
          || |||||| |||||||| |||||||| || ||
       3' gg ccgugg ucuugacu agguucc  ua cg u
             c    -        -c        cg  -a  a
```

The 5' and 3' mature miRNAs are shown in bold. The linear sequence is (SEQ ID NO: 8)
GGUAACACUCAAAAGAUGGCGGCACUUUCACCAGAGAGCAGAAAGUGC

CCCCACAGUUUGAGUGCC.

or hsa-miR-146b-5p. e.g., (SEQ ID NO: 4)
UGAGAACUGAAUUCCAUAGGCUG.

In some embodiments, the oligonucleotide comprises miR-146a-5p, e.g., (SEQ ID NO: 3)
UGAGAACUGAAUUCCAUGGGUU, In some embodiments, the oligonucleotides include one, two, three, four, or more differences from a sequence presented herein, e.g., up to 1%, 2%, 3%, 5%, 10%, 15%, or 20% differences, as long as the oligonucleotide retains the desired function of the reference oligonucleotide (i.e., reduction of angiogenesis, alteration of gene expression levels as shown herein).

The methods can be used in any tissue in which it is desired to reduce angiogenesis, but particularly in cancerous tissues, e.g., in solid tumors. Examples of include carcinoma and sarcoma. A metastatic tumor can arise from a multitude of primary tumor types, including but not limited to those of prostate, colon, lung, breast and liver origin.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, liver, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation. In some embodiments, where the subject has cancer, the method includes administering another treatment described herein in addition to a MLK inhibitor oligonucleotide, or does not include administering a MLK inhibitor.

In addition, the methods can be used to treat angiogenesis-related disorders. As used herein, the term "angiogenesis-related disorder" refers to a number of disease and disorders that are characterized by abnormal vasculature or poor vascularization. Non-limiting examples of angiogenesis-related disorders include: peripheral arterial disease (PAD), macular degeneration, retinopathy, stroke, diabetic limb ulcers, diabetic neuropathy, age-related blindness, chronic wounds, pressure ulcers, Alzheimer's disease, myocardial ischemia, cerebral ischemia, hepatic ischemia, limb ischemia, pulmonary ischemia, renal ischemia, testicular ischemia, intestinal type ischemia, or any organ ischemia. In some embodiments, where the subject has diabetes, the method includes administering another treatment described herein in addition to a miR-146 oligonucleotide, or does not include administering a miR-146 oligonucleotide.

The term "subject" refers to any mammal. In some embodiments, the subject or "subject suitable for treatment" may be a canine (e.g., a dog), feline (e.g., a cat), equine (e.g., a horse), bovine, ovine, caprine, porcine, primate, e.g., a simian (e.g., a monkey, e.g., a marmoset, or a baboon), or an ape (e.g., a gorilla, a chimpanzee, an orangutan, or a gibbon)) or a human; or rodent (e.g., a mouse, a guinea pig, a hamster, or a rat). In some embodiments, the subject or "subject suitable for treatment" may be a non-human mammal, especially mammals that are conventionally used as models for demonstrating therapeutic efficacy in humans (e.g., canine, lapine, murine, porcine, or primate animals) may be employed.

These methods can be used to treat a subject, e.g., a subject with an angiogenesis-related disorder (e.g., a subject with peripheral arterial disease), by administering to the subject a composition as described herein.

As used herein, treating includes "prophylactic treatment" which means reducing the incidence of or preventing (or reducing risk of) a sign or symptom of a disease in a patient at risk for the disease, and "therapeutic treatment", which means reducing signs or symptoms of a disease, reducing progression of a disease, reducing severity of a disease, re-occurrence in a patient diagnosed with the disease.

As used herein in this context, to "treat" means to ameliorate at least one clinical parameter of the disease. In some embodiments, the parameter is blood flow or angiogenesis.

Pharmaceutical Compositions

The methods described herein can include the administration of pharmaceutical compositions and formulations comprising any one or more (e.g., two or three) of the agents described herein as active ingredients, e.g., in some embodiments as the sole active ingredient. In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., Remington: The Science and Practice of Pharmacy, 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives, and antioxidants can also be present in the compositions. In some embodiments, one or more cationic lipids, cationic polymers, or nanoparticles can be included in compositions containing the one or more inhibitory nucleic acids (e.g., compositions containing one or more inhibitory nucleic acids targeting MLK2/3).

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect.

Pharmaceutical formulations of this invention can be prepared according to any method known to the art for the manufacture of pharmaceuticals. Such drugs can contain sweetening agents, flavoring agents, coloring agents, and preserving agents. A formulation can be admixtured with nontoxic pharmaceutically acceptable excipients which are suitable for manufacture. Formulations may comprise one or more diluents, emulsifiers, preservatives, buffers, excipients, etc., and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., inhibitory nucleic acids or sense nucleic acids described herein) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth, and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long-chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents, and one or more sweetening agents, such as sucrose, aspartame, or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil, or coconut oil, or in a mineral oil such as liquid paraffin; or a mixture of these. See e.g., U.S. Pat. No. 5,716,928, describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin, or cetyl alcohol. Sweetening agents can be added to provide a palatable oral preparation, such as glycerol, sorbitol, or sucrose. These formulations can be preserved by the addition of an antioxidant such as ascorbic acid. As an example of an injectable oil vehicle, see Minto, $J.$ $Pharmacol.$ $Exp.$ $Ther.$ 281:93-102, 1997.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters, or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate, and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi, $J.$ $Clin.$ $Pharmacol.$ 35:1187-1193, 1995; Tjwa, $Ann.$ $Allergy$ $Asthma$ $Immunol.$ 75:107-111, 1995). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao, $J.$ $Biomater$ $Sci.$ $Polym.$ $Ed.$ 7:623-645, 1995; as biodegradable and injectable gel formulations, see, e.g., Gao, $Pharm.$ $Res.$ 12:857-863, 1995; or, as microspheres for oral administration, see, e.g., Eyles, $J.$ $Pharm.$ $Pharmacol.$ 49:669-674, 1997.

In some embodiments, the pharmaceutical compounds can be parenterally administered, such as by intravenous (IV) administration or administration into a body cavity, a lumen of an organ, or into the cranium (e.g., intracranial injection or infusion) or the cerebrospinal fluid of a subject. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose, any bland fixed oil can be employed including synthetic mono- or diglycerides. In addition, fatty acids, such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate, and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid or a sense nucleic acid can be made by lyophilizing a solution comprising a pharmaceutical of the invention and a bulking agent, e.g., mannitol, trehalose, raffinose, and sucrose, or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5, but less than 6.5. See, e.g., US2004/0028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989.

The formulations of the invention can be administered for prophylactic and/or therapeutic treatments. In some embodiments, for therapeutic applications, compositions are administered to a subject who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to reduce the number of symptoms or reduce the severity, duration, or frequency of one or more symptoms of a neurodegenerative disorder in a subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age, and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones, *J. Steroid Biochem. Mol. Biol.* 58:611-617, 1996; Groning, *Pharmazie* 51:337-341, 1996; Fotherby, *Contraception* 54:59-69, 1996; Johnson, *J. Pharm. Sci.* 84:1144-1146, 1995; Rohatagi, *Pharmazie* 50:610-613, 1995; Brophy, *Eur. J. Clin. Pharmacol.* 24:103-108, 1983; Remington: The Science and Practice of Pharmacy, 21st ed., 2005). The state of the art allows the clinician to determine the dosage regimen for each individual patient, active agent, and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, and the like. The formulations should provide a sufficient quantity of active agent to effectively treat, prevent or ameliorate conditions, diseases, or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray, or inhalation. Actual methods for preparing parenterally or non-parenterally administrable formulations will be known or apparent to those skilled in the art and are described in more detail in such publications as Remington: The Science and Practice of Pharmacy, 21st ed., 2005.

EXAMPLES

The invention is further described in the following examples, which do not limit the scope of the invention described in the claims.

Materials and Methods

The following materials and methods were used in the Examples below.

Tumor Formation and Tumor Angiogenesis

Figures 5B, 5C:
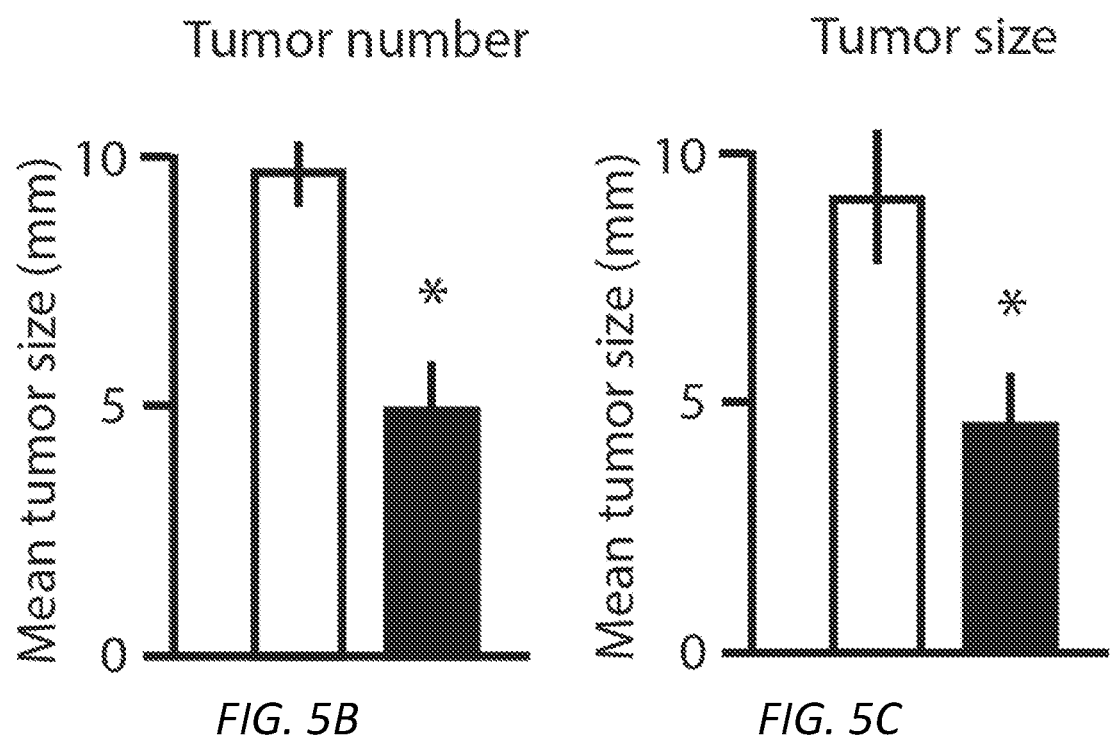
Figure 6:
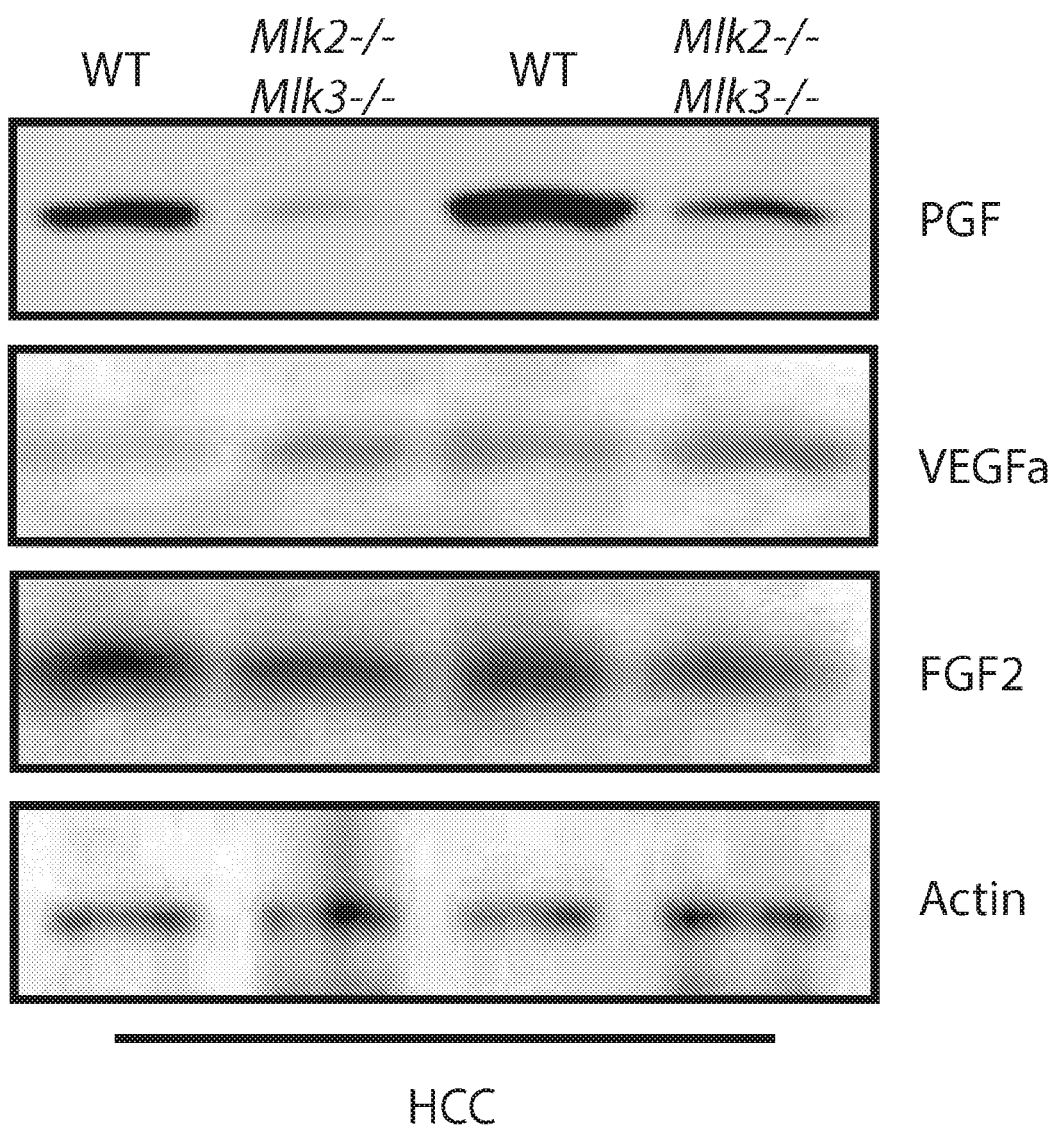
FIG. 6. Pgf, Vegfa, Fgf2 and actin immunoblots from Hepatocellular carcinoma (HCC) tumor of the indicated genotype.
Figure 7A:
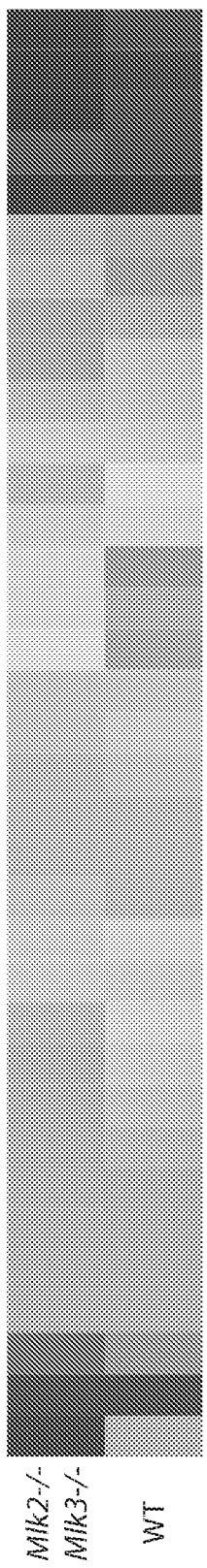
FIGS. 7A-E. MLK is required for the expression of pro-angiogenic factors. (A) Microarray was performed on mRNA isolated from pooled (3 mice) mouse lung endothelial cell (MLEC). (B) mRNA was isolated from mouse lung endothelial cell (MLEC) and qRT-PCR was performed for different angiogenesis related genes after 4 hours post hypoxia treatment. (C) qRT-PCR was performed for different angiogenesis related genes on gastrocnemius muscle from ischemic legs of WT and Mlk2−/− Mlk3−/− mice 6 hours post femoral artery ligation. (D) WT and Mlk2−/− Mlk3−/− mice were injected with carcinogen diethylnitrosamine (DEN) at 3 weeks of age. After 9 months of DEN injection HCC tumors were isolated from liver of WT and Mlk2−/− Mlk3−/− mice and qRT-PCR was performed for different angiogenesis related genes. (E) HCC tumors were isolated and qRT-PCR was performed for different cytokine genes as described in (D). Statistically significant differences between groups are indicated (*, P<0.05).
Figure 7B:
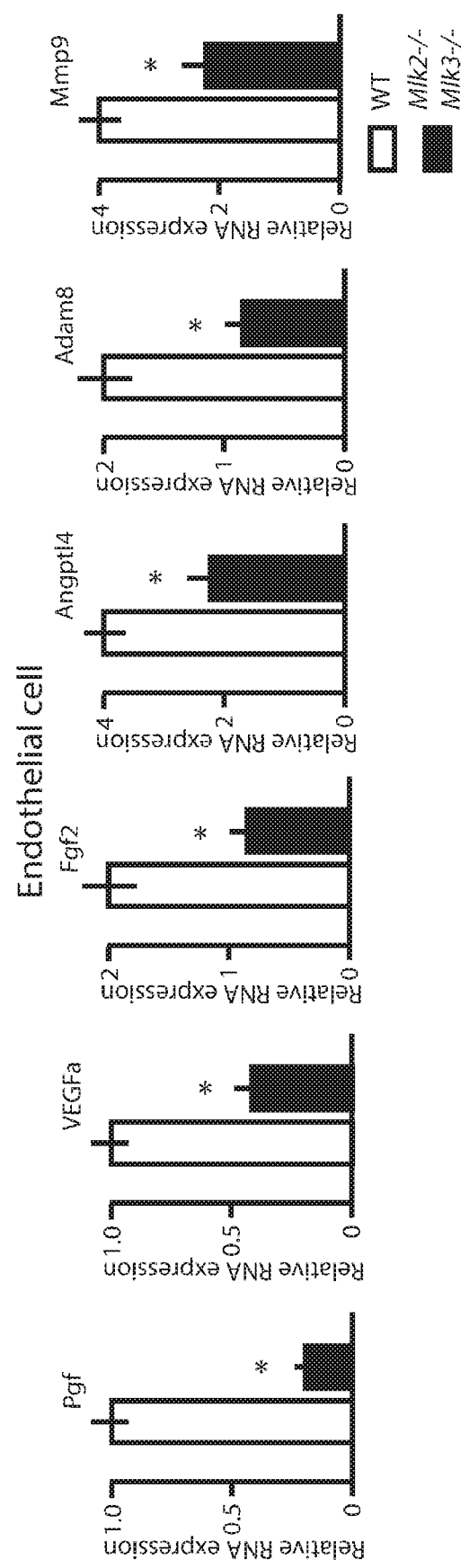
Figure 7C:
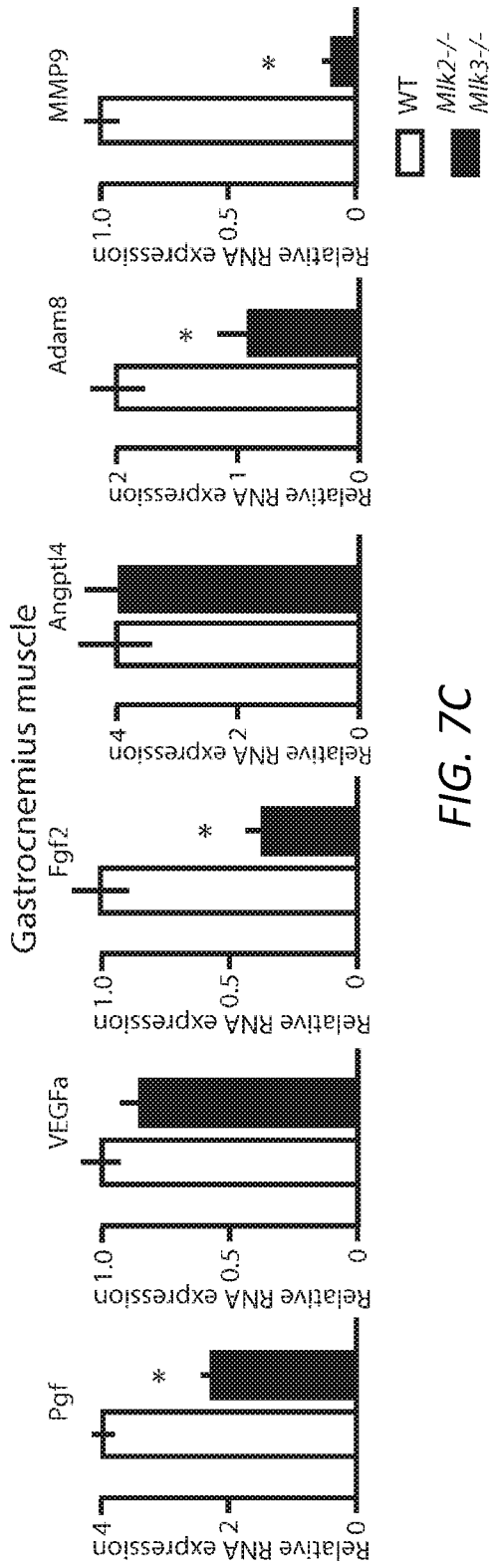
Figure 7D:
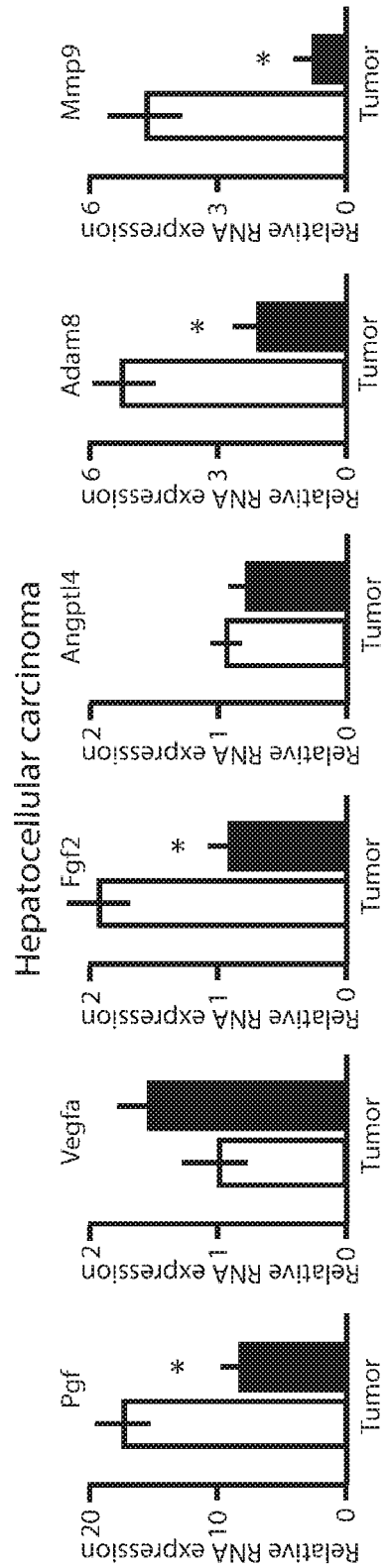
Figure 7E:
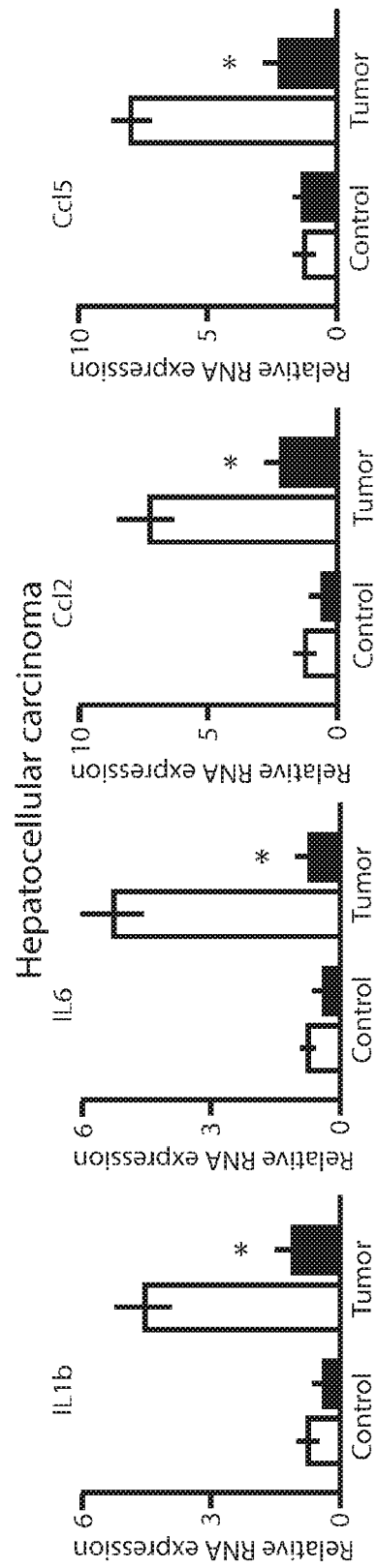

To access the role of MLKs in tumor angiogenesis and endothelial function in vivo we injected MLK2/3−/− mice and Wildtype (WT) control mice with Lewis lung carcinoma cells, (LLC ATCC, 1×106 cells/mouse) in each dorsal flank. Mice were monitored for weight, well-being, tumor formation and tumor diameter (by calipers) every other day. Tumors were harvested at 10-12 d before reaching 1-2 cm or ulceration. For spontaneous tumors we used the DEN-induced hepatocellular carcinoma (HCC) model (FIG. 5A). Intraperitoneal injections of DEN (35 mg/kg BW) were given for 25 weeks followed by euthanasia and liver harvesting for tumor size, incidence, vascularity, and tissue analysis. The HCC model uses slightly younger mice to maximize HCC tumor development. Both tumor models were analyzed for angiogenesis using multiple markers. Capillary density and architecture was examined by CD31/SMA/DAPI immunofluorescence. Protein expression of markers relevant to angiogenesis such as Plgf2, Vegfa, Fgf2, Angptl4, Adam8, Mmp9 and receptors (Flt1, Kdr, Fgfr1, CD51, CD61) were examined by immunoblotting tumor lysates as described. miR-290b were specifically examined by qRT-PCR as in FIG. 8b.

Proliferation and Migration

Primary mouse lung endothelial (MLEC) cells were isologate from WT control and MLK2/3 knockout mice. Using assays to determine endothelial phenotype we assessed proliferation and migration, both characteristics of endothelial cells necessary for angiogenesis. For proliferation we used the MTT assay which utilizes a formazon dye . . . For migration we performed an in vitro scratch assay in both genotype as described.

Hypoxia

Quiescent monolayers of WT and Mlk2/3−/− primary endothelial cell MLECs were exposed to normoxia (21% O2) or hypoxia (1% O2) for 0-24 h in a hypoxia chamber. After exposure cells were immediately harvested and examined for expression of genes by qPCR or immunoblots.

Animals and Hindlimb Ischemia Model

C57BL/6J strain mice were obtained from The Jackson Laboratories. Mice with Mlk2 and Mlk3 [1] gene disruptions have been described previously. The mice were housed in a facility accredited by the American Association for Laboratory Animal Care. All animal studies were approved by the Institutional Animal Care and Use Committee of the University of Massachusetts Medical School.

Either WT or MLK2 and MLK3—null[1] male mice at 10 to 12 weeks of age were anesthetized with intraperitoneal injection of combination of 100 mg/kg ketamine hydrochloride and 5 mg/kg xylazine (Webster Veterinary, Devens, MA) before surgery. Unilateral hindlimb ischemia in the right leg was introduced in the mice as described[2]. Hindlimb tissue perfusion was assessed with either moorLDI2-IR laser-Doppler imaging system or moorFLPI-2 blood flow imager (Moor Instruments, Devon, UK). Blood flow images were obtained under conditions of constant body temperature (36±1.0° C.) and average hindlimb blood flow was expressed as the ratio of ischemic to nonischemic foot flow to account for minor variations in imaging conditions.

Cell Culture and Transfections

Primary mouse endothelial cell (MLEC) from WT control and MLK2/3 knockout mice were isolated as described. Transfection assays were performed using 100 nM small interfering RNA oligonucleotides ON-TARGET plus SMART pool for control (D-001810-10), Jnk3 (MAPK10) (L-045023-00), Creb1 (L-040959-01), Sirtuin1 (L-049440-00) and Nrf1 (L-041037-01) (Thermo Scientific Dharmacon, Lafayette, CO) in DharmaFECT 3 reagent with for 6-8 hours in optimum (Invitrogen). Media was changed to Dulbecco's modified Eagle's medium supplemented with 10% fetal bovine serum, 100 units/ml penicillin, 100 µg/ml streptomycin, and 2 mM L-glutamine (Invitrogen). After 48-72 hours of siRNA treatment cells were exposed with low serum (0.5%) and hypoxia (1% oxygen) for one hour in hypoxia chamber (Billups-Rothenberg Inc.).

To assess Creb activity the cAMP response element (CRE) luciferase assay (Qiagen #CCS-002L) was performed according to manufacture instructions.

RNA Preparation and Quantitative Real-Time Polymerase Chain Reaction

Total RNA was extracted from cells and tissues with the RNeasy Mini Kit (Qiagen) or TRIzol reagent (Invitrogen), and 1 µg of total RNA was reverse transcribed with oligo (dT) primers for cDNA synthesis. The expression of mRNA was examined by quantitative PCR analysis using a QuantStudio™ 6 Flex Real-Time PCR System (Applied Biosystems). Taqman© assays were used to quantitate Pgf, Adam8, Mmp9, Angptl4, Hprt (Mm00446968—m1) and Gapdh (4352339E-0904021) mRNA (Applied Biosystems). The $2^{-\Delta\Delta C_T}$ method is used for relative quantification of gene as described elsewhere[5,6]. reference genes of Hprt and Gapdh have been used to normalize the PCRs in each sample.

Antibodies and Immunoblot Analysis

Cell extracts were prepared using Triton lysis buffer [20 mM Tris (pH 7.4), 1% Triton X-100, 10% glycerol, 137 mM NaCl, 2 mM EDTA, 25 mM b-glycerophosphate, 1 mM sodium orthovanadate, 1 mM phenylmethylsulfonyl fluoride, and 10 µg/mL of aprotinin and leupeptin]. Protein extracts (50 µg of protein) in DTT-containing SDS sample buffer were separated in 10% or 12% SDS-polyacrylamide gels and transferred to Hybond ECL nitrocellulose membranes (GE Healthcare, Piscataway, NJ). Immunecomplexes were detected by Amersham™ Imager 600 using Immobilon Western HRP Substrate (EMD Millipore). Primary antibodies were obtained from Cell Signaling (phospho-ERK1/2 #9101, ERK1/2 #9102, phospho-p38 #9211, p38 #9212, phospho-JNK1/2 #9251 and JNK1/2 #9252), Origene (PGF #TA332424) and Sigma (Actin #A2103).

Microarray

Endothelial cells were pooled from 3 different mice of each group. RNA was isolated using the RNeasy kit (Qiagen). RNA quality (RIN>9) was verified using a Bioanalyzer 2100 System (Agilent Technologies). Microarray was performed at UMASS Genomics Core Facility using GeneChip® Mouse Transcriptome Assay 1.0 by following the manufacturer's instructions (Affimetryx).

Statistical Analysis

All data are expressed as mean±SE and the numbers of independent experiments are indicated. Statistical comparisons were conducted between 2 groups by use of Student t test. A P value<0.05 was considered significant.

Example 1. MLK2/3 are Necessary for Angiogenesis and Tumor Formation

Figure 3A:
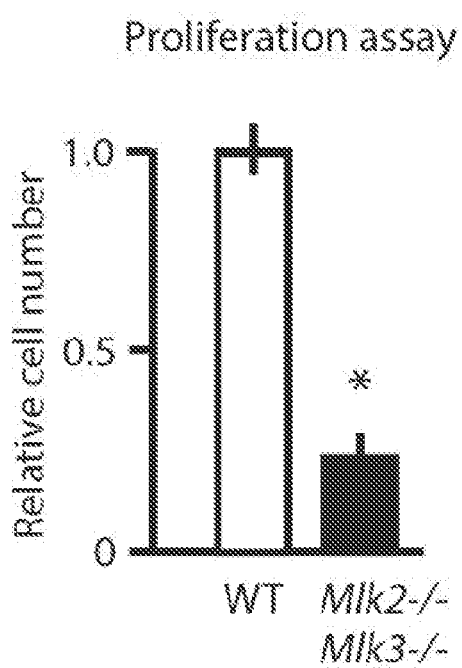
FIGS. 3A-B. MLK deficient endothelial cells exhibit defects in proliferation and migration. (A) MLEC proliferation by genotype at 48 h, N=3/grp, p<0.05. (B) MLEC migration as wound healing in the scratch assay, N=5, p<0.05.
Figure 3B:
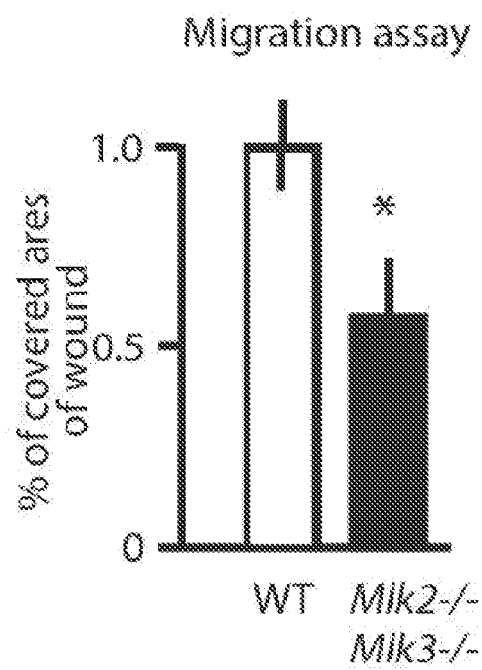
Figure 10:
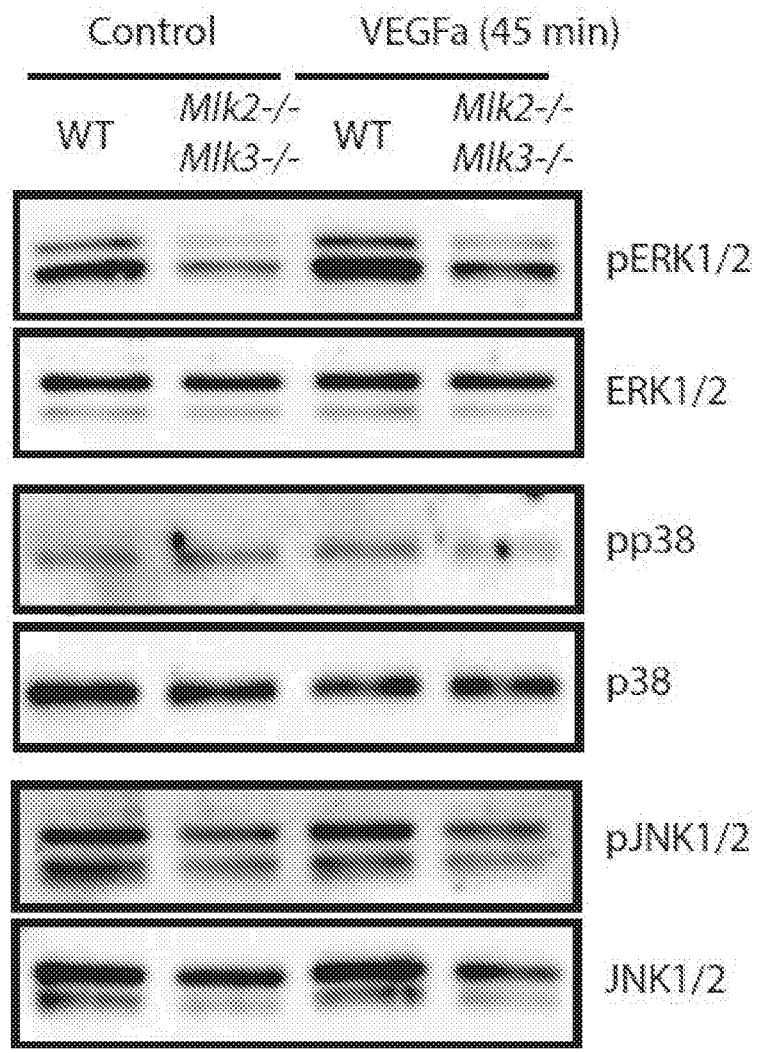
FIG. 10. MLKs and VEGF signaling. MLEC treated with 10 ng/ml VEGFa for 45 minutes followed by immunoblotting as indicated.

In two solid tumor models (hepatocellular carcinoma (HCC), and Lewis Lung Carcinoma (LLC), solid tumor formation and tumor vascularization (FIGS. 4A-B and 5A-C respectively) were significantly inhibited in MLK 2/3 deficient mice, suggesting that targeting MLK is a novel strategy to control solid tumors. In terms of specific endothelial properties, there were significant defects in endothelial cell proliferation (FIG. 3A), migration (FIG. 3B), and VEGF signaling (FIG. 10) in Mlk2/3−/− endothelial cells. Collectively, these data indicate a profound impact of MLK on angiogenic phenotype.

Example 2. MLK2/3 is Required for Hypoxia-Induced Growth Factor Production in the Endothelium MLK2/3 was needed to promote the expression of pro-angiogenic growth factors (VEGF-A, PGF, FGF2) in the endothelium, which is a pre-requisite of neovascularization (FIGS. 7A-E).

Figure 8B:
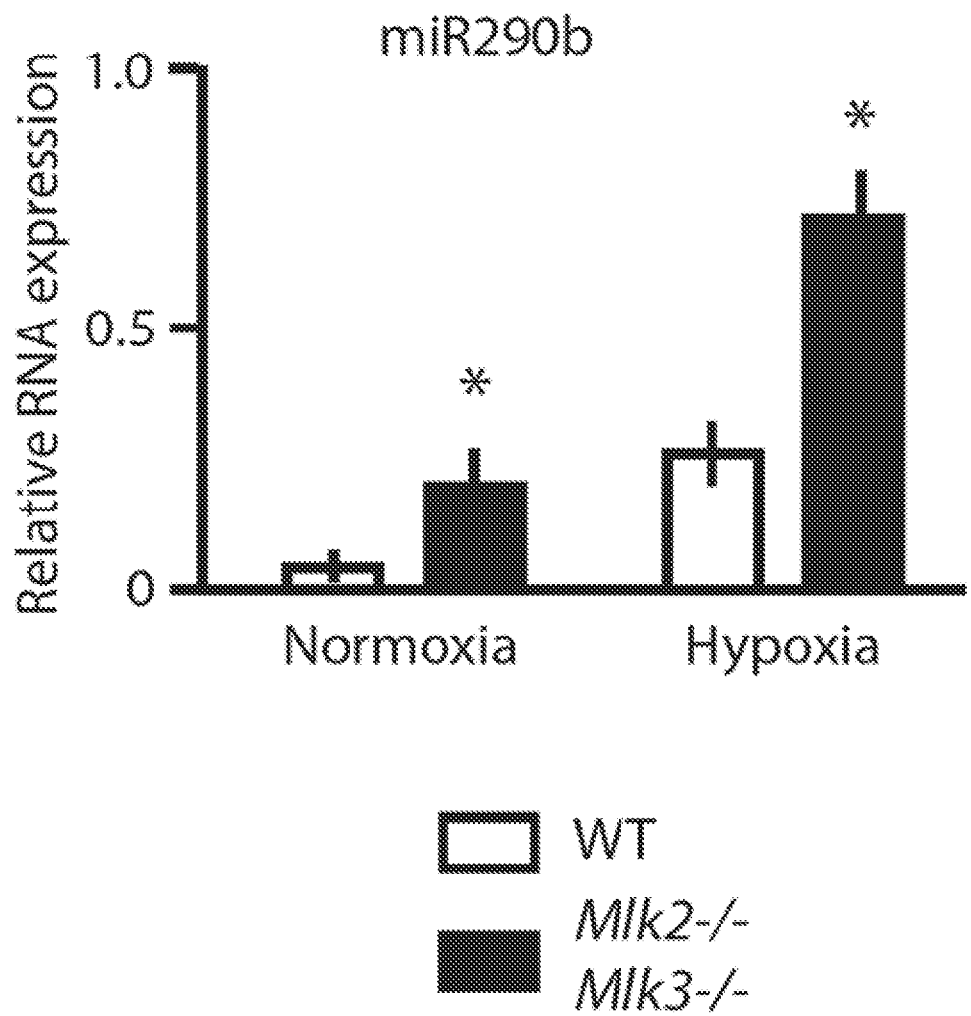
Figure 9A:
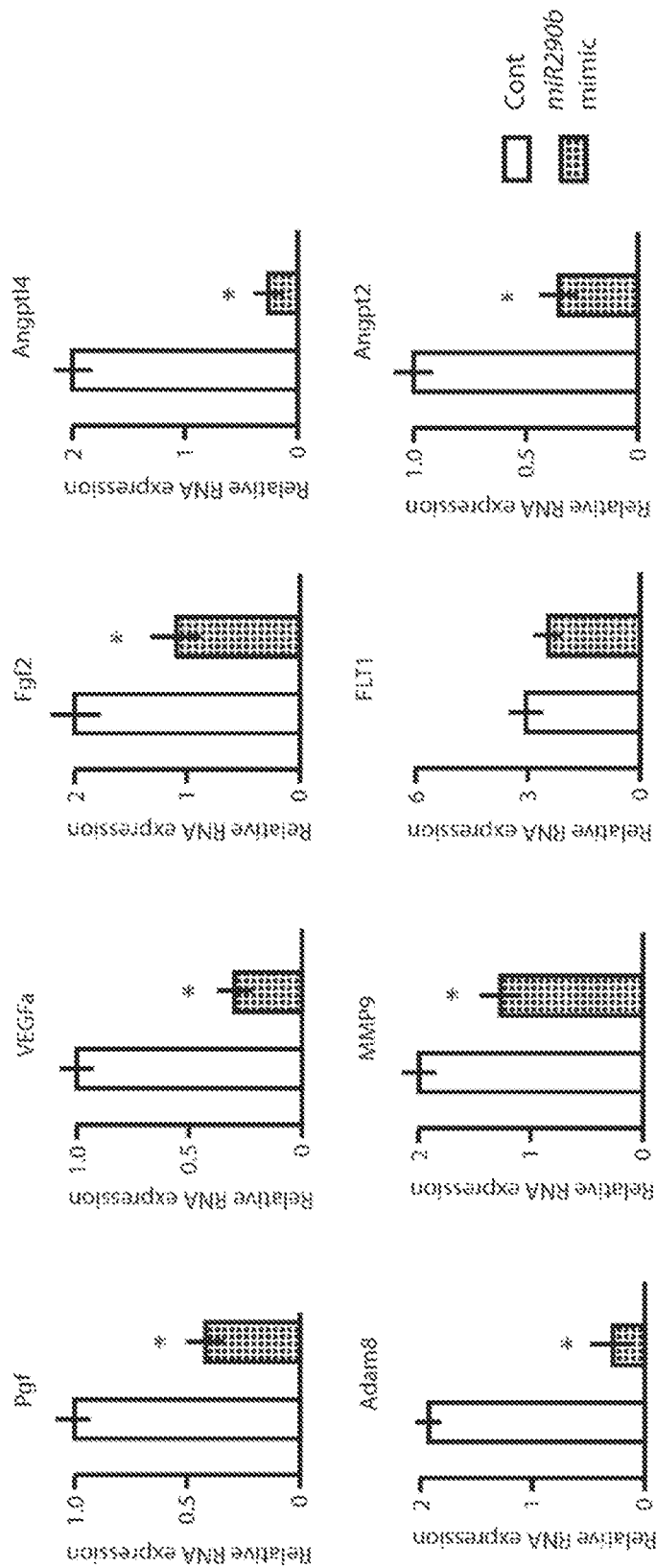
FIGS. 9A-B. MLK regulates pro-angiogenic factors via miR290b micro RNA expression. (A) mRNA was isolated from WT mouse lung endothelial cell (MLEC) treated either with control or miR290b mimic for 48 hours and qRT-PCR was performed for angiogenesis related genes 4 hours post hypoxia. (B) qRT-PCR was performed for angiogenesis-related genes on MLK-deficient mouse lung endothelial cell (MLEC) treated with control or miR290b inhibitor for 48 hours followed 4 hours post hypoxia treatment.
Figure 9B:
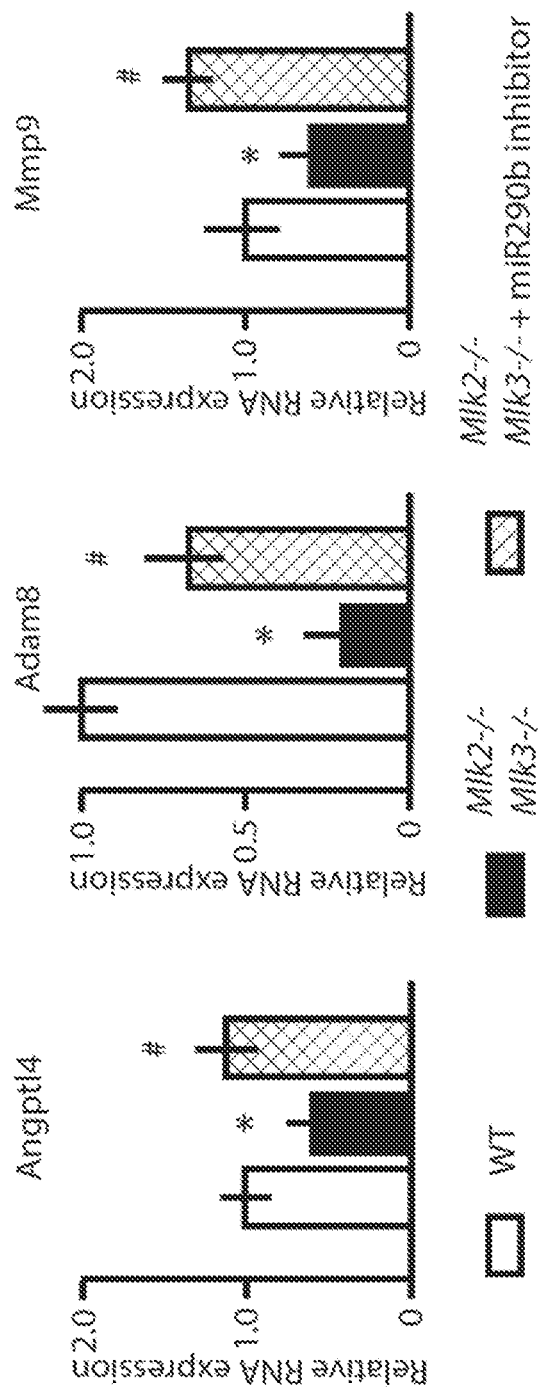

Example 3. miR 290b and miR146a, in Part Mediate the MLK2/3 Angiogenic Response in Endothelial Cells Mlk2/3−/− MLECs exhibited baseline and hypoxia-induced upregulation of miR-290b and miR 146a (FIGS. 8A-B). These two MLK2/3 controlled microRNAs regulated the expression of different growth factors (VEGF-A, PGF, FGF2) in endothelial cells. (FIGS. 9A-B and 11A-D).

Example 4. MLK2/3 Regulates eNOS Expression and Activity

Expression of endothelial nitric oxide synthase (eNOS) is a major determinant of endothelial health and dictates the ability of the endothelium to respond to environmental cues and promotes an angiogenic phenotype. As a master regulator of endothelial function, it was hypothesized that any change in expression or activity of this protein might result in changes in endothelial phenotype. There was a dramatic decrease in eNOS expression at mRNA and protein level in endothelial cells that were MLK2/3 deficient (FIGS. 12A-B).

Example 5. Experimental Metastasis

For experimental metastasis, $1 \times 10^6$ LLC1 cells, were injected into tail vein of WT and MLK2/3 KO mice. After 20 days, lungs were harvested and formalin fixed for histology. The number of metastases per animal was determined in a blinded fashion by counting three H&E-stained coronal lung sections per mouse. We further stained for macrophages in lung tissue (FIGS. 13A, B and C). Furthermore, tumor size, number and incidence were measured; the results are shown in FIGS. 13D-F (WT—White bar; MLK2/3 KO—Black bar).

We also tested the role of MLK inhibitor in Lung tumor formation. As shown in FIGS. 14A and B, $1 \times 10^6$ LLC1 cells, with either MLK inhibitor (URMC-099) or solvent in 200 ul of sterile PBS were injected into the tail vein of WT mice (12-16 week of age). After 20 days of injection Lung was isolated and tumor number were counted (Control—White bar; MLK inhibitor—Black bar).

In addition, control or miR146a mimic (mouse—ugagaacugaauuccauggguu (SEQ ID NO:3) were transfected into primary MLEC cells for 48 hours. Cells were incubated for 90 minutes in a hypoxia chamber in the presence of 1% $O_2$. RNA was isolated and qPCR was performed for genes as described. As shown in FIGS. 15A-H, pro-angiogenic factors like VEGF, Angptl4, Angpt2 and MMP9 were all down-regulated after miR146a mimic treatment. The expression of these pro-angiogenic genes showed a similar pattern as was seen in miR290b treated or MLK2/3 KO cells.

REFERENCES

1. Craige, S. M., M. M. Reif, and S. Kant, *Mixed—Lineage Protein kinases (MLKs) in inflammation, metabolism, and other disease states*. Biochim Biophys Acta, 2016. 1862 (9): p. 1581-6.
2. Gallo, K. A. and G. L. Johnson, *Mixed-lineage kinase control of JNK and p38 MAPK pathways*. Nat Rev Mol Cell Biol, 2002. 3(9): p. 663-72.
3. Widlansky, M. E., et al., *The clinical implications of endothelial dysfunction*. J Am Coll Cardiol, 2003. 42(7): p. 1149-60.
4. Ramo, K., et al., *Suppression of ischemia in arterial occlusive disease by JNK-promoted native collateral artery development*. Elife, 2016. 5.
5. Chadee, D. N., *Involvement of mixed lineage kinase 3 in cancer*. Can J Physiol Pharmacol, 2013. 91(4): p. 268-74.
6. Chen, J. and K. A. Gallo, *MLK3 regulates paxillin phosphorylation in chemokine-mediated breast cancer cell migration and invasion to drive metastasis*. Cancer Res, 2012. 72(16): p. 4130-40.
7. Chen, J., E. M. Miller, and K. A. Gallo, *MLK3 is critical for breast cancer cell migration and promotes a malignant phenotype in mammary epithelial cells*. Oncogene, 2010. 29(31): p. 4399-411.
8. Zhan, Y., et al., *Mixed lineage kinase 3 is required for matrix metalloproteinase expression and invasion in ovarian cancer cells*. Exp Cell Res, 2012. 318(14): p. 1641-8.
9. Zhang, B., et al., *microRNAs as oncogenes and tumor suppressors*. Dev Biol, 2007. 302(1): p. 1-12.
10. Shenouda, S. K. and S. K. Alahari, *MicroRNA function in cancer: oncogene or a tumor suppressor?* Cancer Metastasis Rev, 2009. 28(3-4): p. 369-78.
11. Houbaviy, H. B., et al., *Characterization of a highly variable eutherian microRNA gene*. RNA, 2005. 11(8): p. 1245-57.
12. Marson, A., et al., *Connecting microRNA genes to the core transcriptional regulatory circuitry of embryonic stem cells*. Cell, 2008. 134(3): p. 521-33.
13. Wang, Y., et al., *Embryonic stem cell-specific microRNAs regulate the G1-S transition and promote rapid proliferation*. Nat Genet, 2008. 40(12): p. 1478-83.
14. Medeiros, L. A., et al., *Mir-290-295 deficiency in mice results in partially penetrant embryonic lethality and germ cell defects*. Proc Natl Acad Sci USA, 2011. 108 (34): p. 14163-8.
15. Li, Y., et al., *Functions of miR-146a and miR-222 in Tumor-associated Macrophages in Breast Cancer*. Sci Rep, 2015. 5: p. 18648.
16. Zu, Y., et al., *MiR-146a suppresses hepatocellular carcinoma by downregulating TRAF6*. Am J Cancer Res, 2016. 6(11): p. 2502-2513.
17. Chen, G., et al., *miR-146a inhibits cell growth, cell migration and induces apoptosis in non-small cell lung cancer cells*. PLoS One, 2013. 8(3): p. e60317.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a solid tumor in a subject, the method comprising administering a composition comprising a miR-371 oligonucleotide comprising SEQ ID NO: 1 or SEQ ID NO: 2, wherein the composition is administered locally to the tumor or to the vasculature of the tumor, wherein the composition is administered in an amount sufficient to inhibit angiogenesis in the tumor, and wherein the solid tumor is a lung carcinoma.

2. The method of claim 1, wherein the miR-371 oligonucleotide comprises SEQ ID NO: 1.

3. The method of claim 1, wherein the miR-371 oligonucleotide comprises SEQ ID NO:2.

* * * * *

SEQUENCE LISTING

<160> NUMBER OF SEQ ID NOS: 8

<210> SEQ ID NO 1
<211> LENGTH: 22
<212> TYPE: RNA
<213> ORGANISM: Homo sapiens

```
<400> SEQUENCE: 1
acucaaaaga uggcggcacu uu                                              22

<210> SEQ ID NO 2
<211> LENGTH: 20
<212> TYPE: RNA
<213> ORGANISM: Homo sapiens

<400> SEQUENCE: 2
acucaaacug uggggggcacu                                                20

<210> SEQ ID NO 3
<211> LENGTH: 22
<212> TYPE: RNA
<213> ORGANISM: Homo sapiens

<400> SEQUENCE: 3
ugagaacuga auccaugggg uu                                              22

<210> SEQ ID NO 4
<211> LENGTH: 23
<212> TYPE: RNA
<213> ORGANISM: Homo sapiens

<400> SEQUENCE: 4
ugagaacuga auccauagg cug                                              23

<210> SEQ ID NO 5
<211> LENGTH: 67
<212> TYPE: RNA
<213> ORGANISM: Homo sapiens

<400> SEQUENCE: 5
guggcacuca aacugugggg gcacuuucug cucucuggug aaagugccgc caucuuuga      60 guguuac                                                               67

<210> SEQ ID NO 6
<211> LENGTH: 66
<212> TYPE: RNA
<213> ORGANISM: Homo sapiens

<400> SEQUENCE: 6
gguaacacuc aaaagauggc ggcacuuuca ccagagagca gaaagugccc ccacaguuug     60
agugcc                                                                66

<210> SEQ ID NO 7
<211> LENGTH: 99
<212> TYPE: RNA
<213> ORGANISM: Homo sapiens

<400> SEQUENCE: 7
ccgaugugua uccucagcuu ugagaacuga auccauggg uugugucagu gucagaccuc      60
ugaaauucag uucuucagcu gggauaucuc ugucaucgu                            99

<210> SEQ ID NO 8
<211> LENGTH: 66
<212> TYPE: RNA
<213> ORGANISM: Homo sapiens

<400> SEQUENCE: 8
```

```
gguaacacuc aaaagauggc ggcacuuuca ccagagagca gaaagugccc ccacaguuug    60
agugcc                                                              66
```